US011524313B2

(12) United States Patent
Botton et al.

(10) Patent No.: US 11,524,313 B2
(45) Date of Patent: Dec. 13, 2022

(54) SYSTEM FOR DISPENSING SUBSTANCE

(71) Applicants: David Botton, Hallandale Beach, FL (US); April Krawiecki, Hollywood, FL (US)

(72) Inventors: David Botton, Hallandale Beach, FL (US); April Krawiecki, Hollywood, FL (US)

(*) Notice: Subject to any disclaimer, the term of this patent is extended or adjusted under 35 U.S.C. 154(b) by 46 days.

(21) Appl. No.: 17/339,580

(22) Filed: Jun. 4, 2021

(65) Prior Publication Data

US 2021/0379618 A1 Dec. 9, 2021

Related U.S. Application Data

(60) Provisional application No. 63/034,504, filed on Jun. 4, 2020.

(51) Int. Cl.
| | | |
|---|---|---|
| *B05C 1/08* | (2006.01) | |
| *A41D 20/00* | (2006.01) | |
| *A61L 2/26* | (2006.01) | |
| *B05C 3/18* | (2006.01) | |

(52) U.S. Cl.
CPC ............... *B05C 1/08* (2013.01); *A41D 20/00* (2013.01); *A61L 2/26* (2013.01); *B05C 3/18* (2013.01); *A41D 2400/00* (2013.01); *A61L 2202/15* (2013.01)

(58) Field of Classification Search
None
See application file for complete search history.

(56) References Cited

U.S. PATENT DOCUMENTS

| | | | | | |
|---|---|---|---|---|---|
| 1,609,481 | A | * | 12/1926 | McCarthy | A44C 5/003 132/294 |
| 3,009,614 | A | * | 11/1961 | Humphner | A44C 5/003 224/241 |
| 3,202,331 | A | * | 8/1965 | McKinstrie | B63C 11/02 224/241 |
| 3,244,331 | A | * | 4/1966 | Kharasch | B65D 83/50 222/394 |
| 4,768,688 | A | * | 9/1988 | Harrigan | A45D 34/00 63/3 |
| 4,977,625 | A | * | 12/1990 | Charters, III | A41D 13/088 D29/120.2 |
| 5,957,347 | A | * | 9/1999 | White | A63B 21/0602 224/148.1 |
| 7,316,332 | B2 | | 1/2008 | Powers et al. | |

(Continued)

FOREIGN PATENT DOCUMENTS

| | | |
|---|---|---|
| CN | 20191930222 | 5/2020 |
| KR | 1020070056148 | 12/2008 |

*Primary Examiner* — Jethro M. Pence
(74) *Attorney, Agent, or Firm* — Derek Fahey, Esq.; The Plus IP Firm, PLLC

(57) ABSTRACT

A wearable system for dispensing a substance is disclosed. The wearable system includes a base element, at least one reservoir surface defining a reservoir disposed in the base element, at least one first opening disposed along on an outward facing portion of the base element and providing fluid communication with the reservoir, and a rolling element disposed in the at least one first opening such that a first portion of the rolling element is outside the base element and a second portion of the rolling element is inside the base element.

20 Claims, 11 Drawing Sheets

(56) References Cited

U.S. PATENT DOCUMENTS

| | | | |
|---|---|---|---|
| 7,766,193 B2* | 8/2010 | Stollmann | A44C 5/003 224/219 |
| 8,708,194 B2* | 4/2014 | Pascatore | B65D 83/005 222/386 |
| 8,950,632 B2* | 2/2015 | Ciavarella | A61L 2/22 224/148.2 |
| 9,089,190 B2* | 7/2015 | Booker | A61J 1/035 |
| 9,578,935 B2* | 2/2017 | Horgan | A45D 34/00 |
| 9,693,607 B2* | 7/2017 | Imbriani | A44C 5/003 |
| 9,888,816 B1 | 2/2018 | Shaukat et al. | |
| 9,943,159 B1 | 4/2018 | Novikova | |
| 10,028,624 B1 | 7/2018 | Robinson | |
| 10,123,607 B1* | 11/2018 | Hardy | A45D 40/261 |
| 10,362,907 B2* | 7/2019 | Holleron | A47K 5/05 |
| 10,413,025 B1 | 9/2019 | Cwalinski et al. | |
| 10,646,076 B2* | 5/2020 | Shaukat | A44C 5/20 |
| 10,952,568 B2* | 3/2021 | Matthews | A45D 40/00 |
| 11,176,802 B1* | 11/2021 | Robinson | G06F 1/163 |
| 11,191,395 B2* | 12/2021 | Shaukat | B05B 11/0054 |
| 11,197,588 B1* | 12/2021 | Thibideau | A47K 5/1217 |
| 11,304,570 B1* | 4/2022 | Shaukat | A47K 5/1217 |
| 11,406,789 B2* | 8/2022 | Bimle | A61M 15/08 |
| 2006/0126444 A1* | 6/2006 | Ellner | A45F 5/00 368/246 |
| 2006/0219742 A1* | 10/2006 | Chen | A45D 33/33 224/267 |
| 2008/0251539 A1* | 10/2008 | Yapaola | A47K 5/10 222/175 |
| 2009/0032049 A1 | 2/2009 | Rabin | |
| 2011/0155765 A1* | 6/2011 | Properzi | A47K 5/1201 222/401 |
| 2011/0167536 A1* | 7/2011 | Kellerhals | A45C 1/04 224/267 |
| 2012/0138637 A1 | 6/2012 | Ciavarella et al. | |
| 2013/0104599 A1* | 5/2013 | Beldiman | A44C 5/003 63/1.14 |
| 2013/0251436 A1* | 9/2013 | Morrow | A45D 34/00 401/6 |
| 2014/0117060 A1* | 5/2014 | Colone | A44C 5/003 224/219 |
| 2015/0129616 A1* | 5/2015 | Ciavarella | B05B 11/00412 222/95 |
| 2015/0158042 A1* | 6/2015 | Parker | A44C 15/005 222/183 |
| 2015/0216367 A1* | 8/2015 | Barbier | B05B 11/048 222/1 |
| 2015/0359321 A1* | 12/2015 | Wu | G09F 3/005 224/219 |
| 2016/0044997 A1 | 2/2016 | Horgan | |
| 2017/0119109 A1 | 5/2017 | Imbriani | |
| 2017/0156454 A1* | 6/2017 | Abadi | A44C 5/0053 |
| 2017/0216519 A1 | 8/2017 | Vouillamoz et al. | |
| 2018/0070699 A1* | 3/2018 | Acosta | A45F 5/00 |
| 2018/0071466 A1 | 3/2018 | White et al. | |
| 2018/0206682 A1* | 7/2018 | Robinson | A47K 5/1202 |
| 2019/0038087 A1 | 2/2019 | Holleron | |
| 2020/0268217 A1* | 8/2020 | Shaukat | A47K 5/1204 |
| 2022/0233028 A1* | 7/2022 | Shaukat | A47K 5/1217 |

* cited by examiner

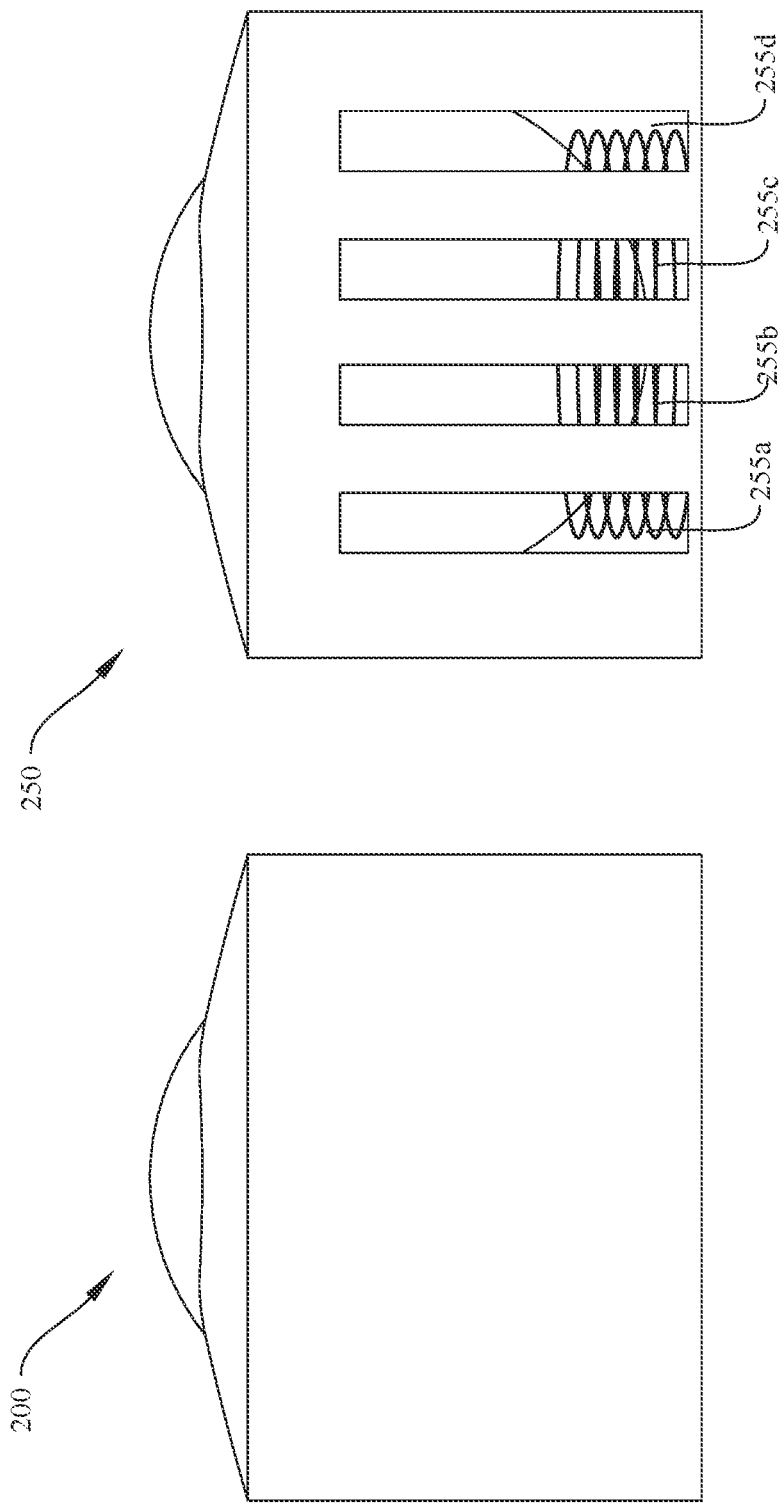

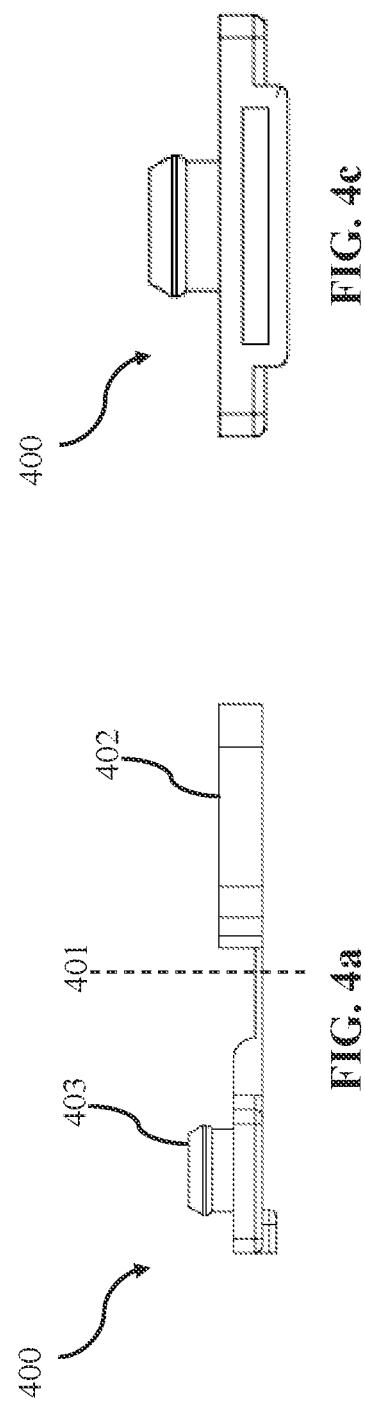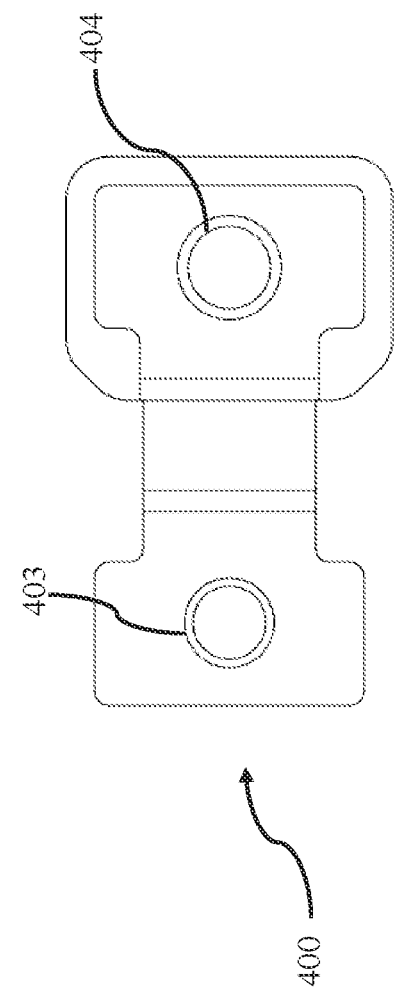

SYSTEM FOR DISPENSING SUBSTANCE

CROSS-REFERENCE TO RELATED APPLICATIONS

This patent application claims priority to U.S. provisional patent application No. 63/034,504, filed on Jun. 4, 2020, and entitled, "SYSTEM FOR DISPENSING SUBSTANCE," which is hereby incorporated by reference in its' entirety.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISC

Not applicable.

TECHNICAL FIELD

The present invention relates to dispensers, and more specifically, to the field of systems for dispensing substances.

BACKGROUND

The Centers for Disease Control and Prevention (CDC) states that many diseases and conditions are spread by individuals not taking precautionary measures, such as properly disinfecting their hands after coming into contact with surfaces, resulting in applicable germs spreading in a rampant manner. In order to combat the rampant spread of these germs, it has become common for individuals to carry small containers filled with disinfecting substances such as hand sanitizers and/or use portable packets of disinfecting wipes. However, during time periods where an applicable disease, virus, or other germ is spread in a rampant manner, hand sanitizers and other common portable disinfecting agents become rather difficult to obtain due to increased demand.

Furthermore, although disinfecting mechanisms may be available in small portable containers, these containers become burdensome due to issues associated with storage and accessibility when performing activities such as exercising. For example, it is common for an individual going for a run/jog to carry as few items on them as possible. There are currently few methods available for the individual to conveniently apply disinfecting substances to their hands without carrying the portable container on them, and this method results in disruption of the workout in some capacity. In addition, individuals performing various exercises frequently engage in movements that require the use of at least one of their hands. Trying to apply disinfecting substances or any other common substance such as moisturizer during these various exercises increases the difficulty of the task altogether.

Wearable technologies such as smartwatches and wristbands have become common for individuals to wear while performing various daily activities allowing individuals to significantly increase the amount of metrics received relating to their body and perform various tasks associated with their daily lives while reducing the amount of items that need to be physically carried.

Therefore, there exists a need for improvements over the prior art and more particularly for a more efficient way to dispense substances in a manner that does not require additional items to be carried by an individual.

SUMMARY

A wearable system for dispensing a substance is disclosed. Generally, the system comprises a base element, at least one reservoir surface defining a reservoir disposed in the base element, at least one first opening disposed along on an outward facing portion of the base element and providing fluid communication with the reservoir, and a rolling element disposed in the at least one first opening such that a first portion of the rolling element is outside the base element and a second portion of the rolling element is inside the base element.

The wearable system may also comprise a biasing element disposed in the reservoir, the biasing element having a biasing element first end and a biasing element second end. In one embodiment, the biasing element first end abuts the at least one reservoir surface. In one embodiment, the biasing element second end abuts the second portion of the rolling element such that the rolling element is continually biased outward to a first position. In one embodiment, each rolling element moves into a second position when a threshold amount of external force acts on the rolling element.

In one embodiment, at least one socket structure is used in the first opening(s). In one embodiment, a retaining wall is defined by each of the at least one socket structure. In one embodiment, a third portion of the rolling element abuts the retaining wall of each of the at least one socket structure when (i) the at least one socket structure is disposed within the at least one first opening, (ii) the rolling element is disposed within the at least one socket structure and (iii) the rolling element is in a first position.

In one embodiment, the base element is an elongated band. In one embodiment, the base element comprises a second opening disposed on the outward facing portion of the base element, the second opening providing fluid communication with the reservoir. In one embodiment, a cover is configured for closing the second opening. In one embodiment, the cover is hingedly in attachment with the base element. In one embodiment, the elongated band has a first end and a second end, wherein the first end of the elongated band is configured to removably attach to the second end of the elongated band to form a looped element to be worn on a user's wrist.

BRIEF DESCRIPTION OF THE DRAWINGS

The accompanying drawings, which are incorporated in and constitute part of this specification, illustrate embodiments of the invention and together with the description, serve to explain the principles of the disclosed embodiments. The embodiments illustrated herein are presently preferred, it being understood, however, that the invention is not limited to the precise arrangements and instrumentalities shown, wherein:

FIG. 2c is a side view of the socket structure from FIGS. 2a-2b;

FIG. 2d is a side view of a socket structure with a plurality of recessed portions in the retaining walls for facilitating the transfer of the substance from the reservoir to the socket reservoir;

FIG. 4a is a side view of a refill port for use with a wearable system, according to an example embodiment;

FIG. 4b is a top view of the refill port of FIG. 4a;

FIG. 4c is a second side view of a refill port of FIG. 4a;

FIG. 5b is a bottom view of the snap element of FIG. 5a;

FIG. 5c is a second side view of the snap element of FIG. 5a.

DETAILED DESCRIPTION

Figure 1A:
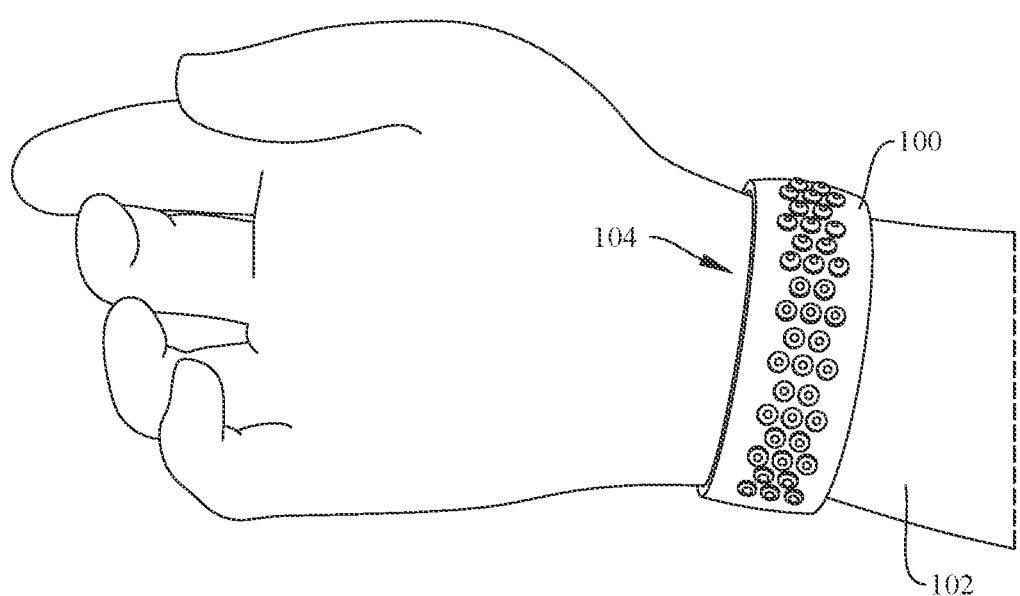
FIG. 1a is an exemplary wearable system for dispensing a substance donned by a user according to an example embodiment of the present invention.

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions or modifications may be made to the elements illustrated in the drawings, and the methods described herein may be modified by substituting reordering or adding additional stages or components to the disclosed methods and devices. Accordingly, the following detailed description does not limit the disclosed embodiments. Instead, the proper scope of the disclosed embodiments is defined by the appended claims.

The disclosed embodiments improve upon the problems with the prior art by providing a system for dispensing substances that prevent rampant spread of viruses, bacteria, and germs along with simultaneously eliminating the need for users to carry and come into contact with portable containers including said substances. The disclosed embodiments also improve over the prior art by providing integration of storage, dispensing, and self-cleaning configurations within wearable technologies (e.g., wristbands, smartwatches, clothes, pendants, bracelets) and other structures in need of coming into contact with said substances (keypads, mice, keyboards, cellphones, cases, accessories, etc.) for various purposes such as disinfecting. The present embodiment utilizes a base element, a reservoir defined by at least one reservoir surface, and at least one first opening to dispense the substance by the user simply applying a force to the components associated with the first opening, thereby allowing the substance to be released on the surface of outer facing surface the base element. Additionally, the present invention may be configured to apply any other applicable substance to an individual or an applicable surface in a convenient and efficient manner; thus, reducing the number of belongings an individual must carry on them.

Referring now to FIG. 1a, a wearable system for dispensing a substance (100) is presented according to an example embodiment of the present invention. As illustrated, system (100) is configured to be donned by a user (102) via a base element (104) configured to be in direct contact with at least one body part of user (102). It is to be understood that base element (104) may be a band, bracelet, bangle, strap, necklace, garment, pendant, jewelry, or any other applicable mechanism configured to be directly affixed to user (102) in a convenient and easily portable manner.

In one embodiment, base element (104) is a substantially ring-shaped element configured to be worn around the wrist of user (102) as illustrated in FIG. 1a. In one embodiment, base element (104) may be a housing and/or planar surface configured to be affixed or attached to at least one mechanism comprising one or more surfaces configured to be disinfected. For example, system (100) may be integrated into a pad, mouse pad, plaque, or any other applicable surface, wherein base element (104) may be stationary but configured to allow the dispensed substance to come into direct contact with the surface. However, in a preferred embodiment, base element (104) is a wristband configured to be provided in a variety of shapes, sizes, and/or dimensions and is further configured to support various configurations. Base element (104) may be made of many materials including, but not limited to, plastic, silicone rubber, natural rubber, neoprene, polyurethane, nylon, carbon steel, stainless steel, aluminum, titanium, other metals or alloys, composites, ceramics, polymeric materials (polycarbonates), or any combination thereof. It is to be understood that system (100) is designed and configured to be a self-cleaning system wherein base element (104) utilizes its components to disinfect its applicable surfaces.

In one embodiment, base element (104) is an elongated band (see FIGS. 1a-1f). In one embodiment, the elongated band has a first end and a second end, where the first end of the elongated band is configured to removably attach to the second end of the elongated band to form a looped element to be worn on a user's wrist. The looped element may be secured by a buckle (see FIG. 1f) or other securing device. In one example, a snap element is used, such as the snap element (500) shown in FIGS. 1e and 5a-5c. The snap element (500) may be placed at an opposing end on the elongated band of receiving portions (510) such as those shown in FIG. 1c. Due to the flexible nature of the base element, a threshold amount of force may be applied to the snap element (500) after looping the band to secure the band in the looped position. Other mechanisms and devices for securing the elongated band in a looped configuration may be used and are within the spirit and scope of the invention.

Figure 1B:
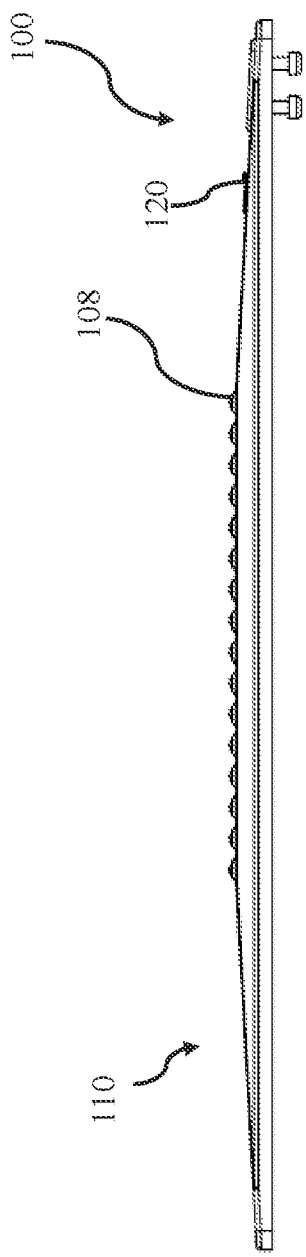
FIG. 1b is a planar side-view wearable system for dispensing a substance, according to an example embodiment.
Figure 1C:
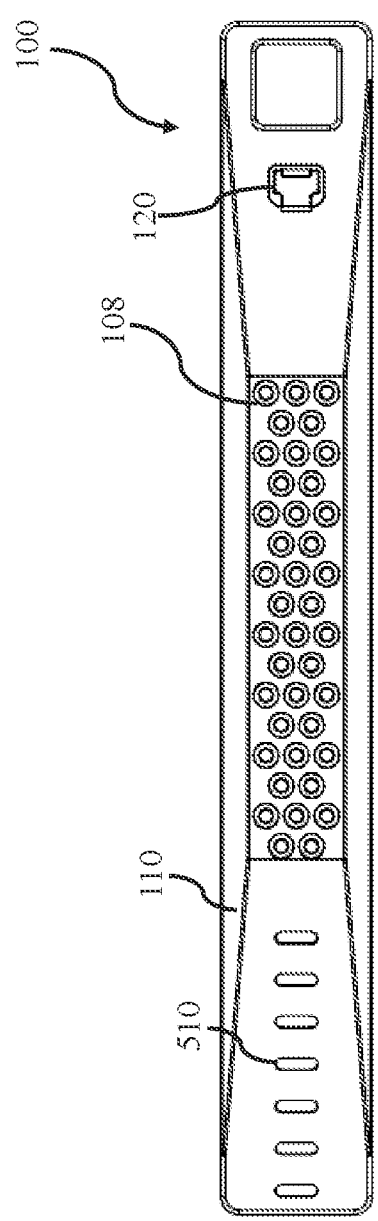
FIG. 1c is a planar top-view (outer surface depicted) wearable system for dispensing a substance, according to an example embodiment.

Referring now to FIGS. 1b-1f, multiple views of an embodiment of a wearable system (100) are shown. As illustrated in FIG. 1b (planar side view) and FIG. 1c (planar top view), the wearable system (100) includes the aforementioned base element (104) and a plurality of openings (108) disposed along on an outward facing portion (110) of the base element (104). As will become more apparent from the foregoing description, the openings (108) are in fluid communication with a reservoir (107), such as the one shown in FIG. 1d. The openings (108) allow for a substance (e.g., a fluid such as a sanitizer) to be dispensed from the reservoir (107) at the will of the user. In this manner, the wearable system provides on-demand access to dispensing a substance at the convenience of the user (102).

It is to be understood that substance (112) may include, but is not limited to, a disinfecting agent, anti-bacterial agent, moisturizer, lip balm, fragrance, ointment, combination thereof, or any other applicable type of substance that is configured to be applied to user (102) for disinfecting and/or moisturizing purposes.

The reservoir (107) may be replenished as the user depletes the reservoir of the substance during use. In particular, the reservoir may be replenished by a second opening (120) disposed on the outward facing portion of the base element (104), the second opening (120) providing fluid communication with the reservoir (107). An example of such a second opening (120) is shown by FIGS. 4a-4c, which show a refill port (400). The refill port (400) may be snapped about axis (401) to open and close the refill port (400). Refill port (400) may comprise at least two portions, a cap portion (402) and a port portion (403). The cap portion (402) includes a recessed portion (404) that encapsulates the port portion (403) when snapped into a closed position. Refill port (400) may be considered as a cover (400) that is configured for closing the second opening (120). The cover (400) may be hingedly in attachment with the base element (100) as illustrated by FIGS. 4a-4c. In this regard, the term, "in attachment" may mean in direct contact with the base element, or indirect contact with the base element. For instance, a gasket, or other intermediate object between the cover and the base element may be used in the attachment.

Figure 1D:
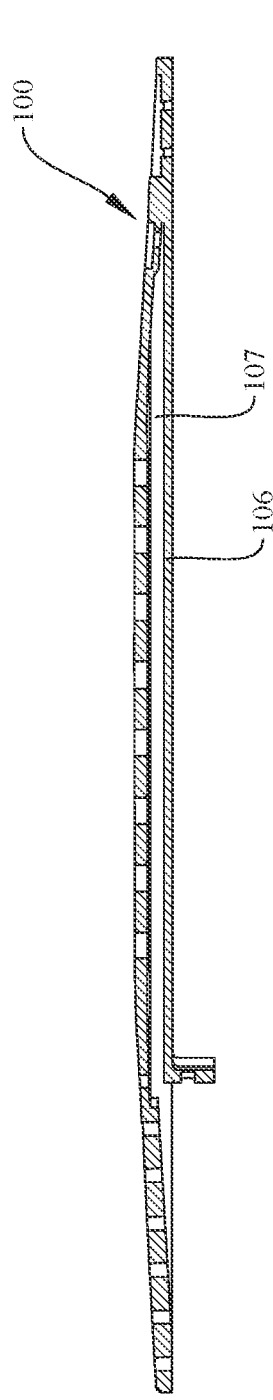
FIG. 1d is a planar side- and cutaway-view of a wearable system for dispensing a substance, detailing a reservoir surface and reservoir, according to an example embodiment.
Figure 1E:
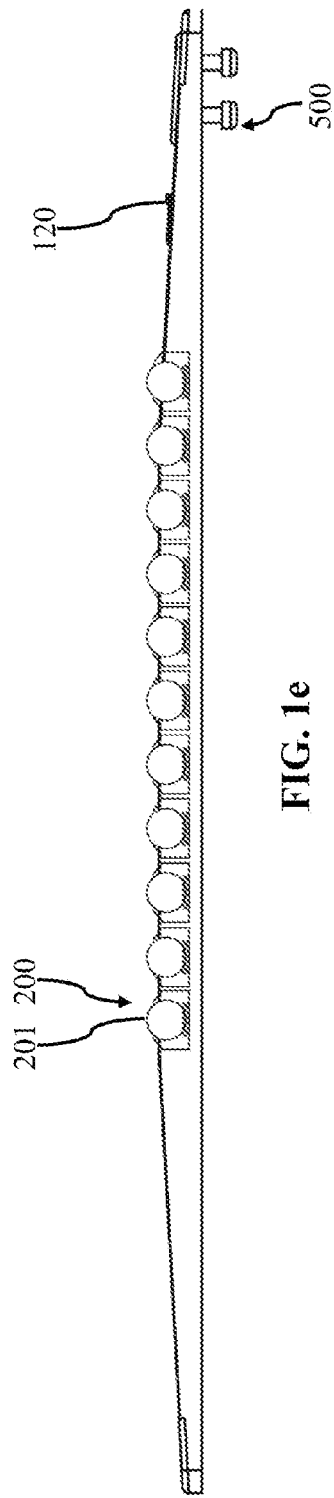
FIG. 1e is a planar side- and cutaway-view of a wearable system for dispensing a substance, detailing a plurality of socket structures inside the wearable system, according to an example embodiment.
Figure 1F:
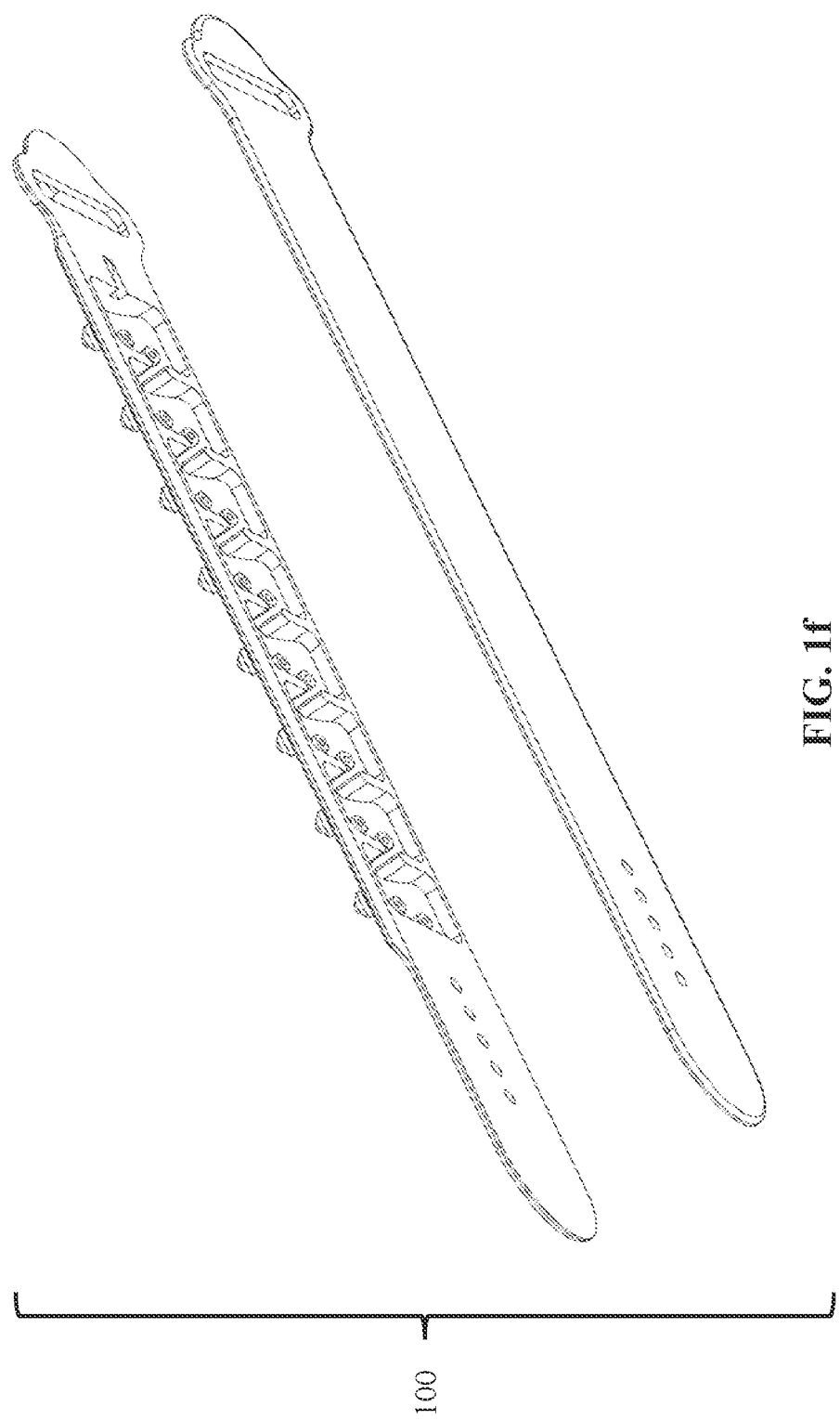
FIG. 1f is a three-dimensional perspective exploded view of a wearable system for dispensing a substance, according to an example embodiment.
Figure 1G:
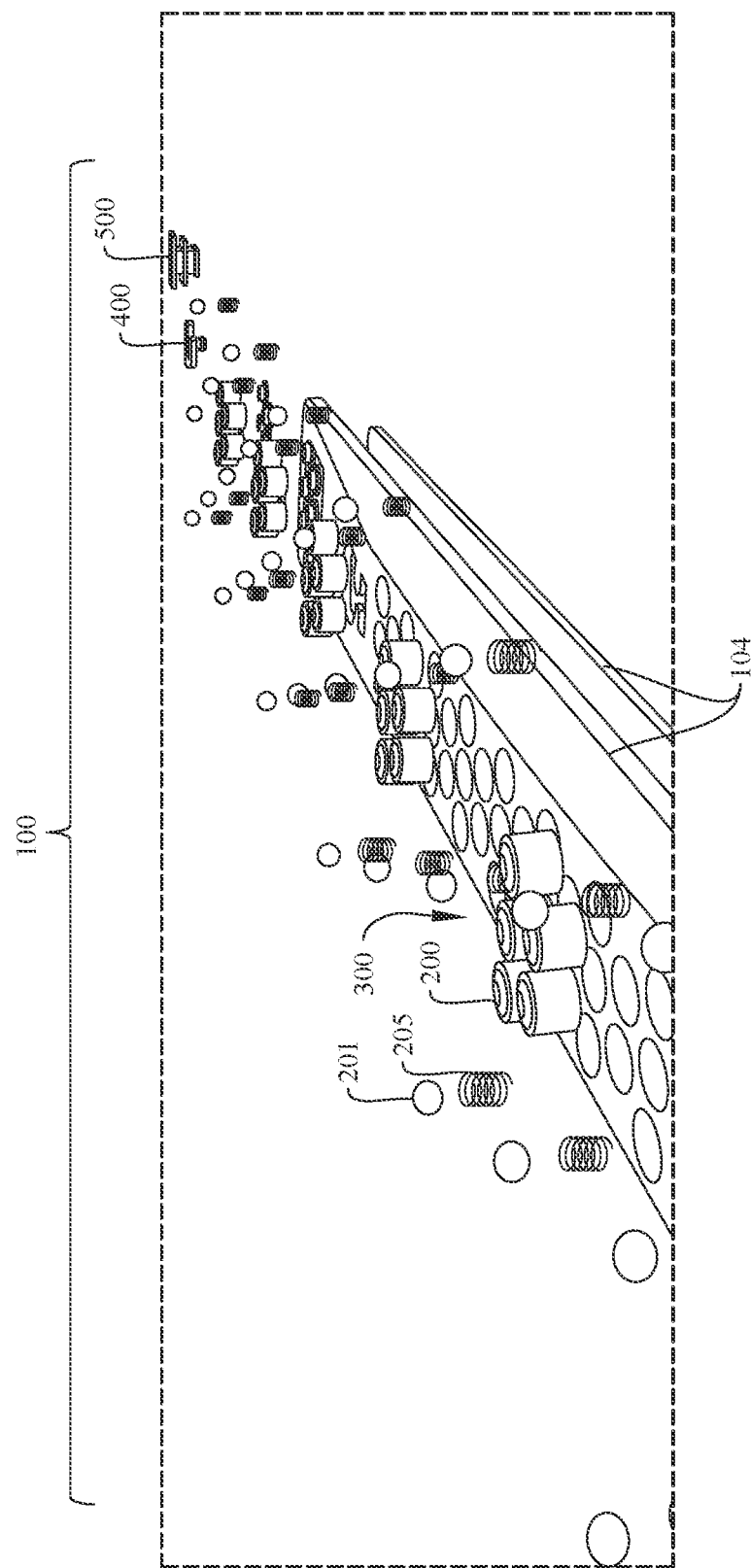
FIG. 1g is a perspective exploded view of a wearable system for dispensing a substance, according to an example embodiment.

As noted above, the system (100) includes a base element (104). The base element (104) may be a monolithic object or may be comprised of multiple parts. For instance, FIGS. 1f and 1g show a system (100) comprised of two portions. The first portion (outward facing portion) is capable of attaching with the second portion (inward facing portion). In an alternative embodiment, the first portion may be hingedly attached to the second portion. In this manner, the first portion may simply be folded into the second portion about the hinge (e.g., a seam along the length of the elongated band or other base element) to form the base element. Other arrangements, such as multiple portions (e.g., three or more) may be used and are within the spirit and scope of the invention. However, a base element (104) comprising a first portion and a second portion is understood to be an advantageous design due to the simplicity in manufacturing the base element (104).

The wearable system (100) includes at least one reservoir surface (106) defining the aforementioned reservoir (107) disposed in the base element and providing fluid communication with the at least one reservoir surface (106). In one aspect, the reservoir surface (106) may be a continuous portion disposed inside of the base element (104), such as illustrated by FIG. 1d. As illustrated in FIG. 1d, the wearable system (100) shows a reservoir surface (106) that is defined by the perimeter of the black region. The resulting reservoir is the black region (107) and is capable of storing the substance that the system dispenses. As will be described in greater detail below, a wearable system (100) may include a plurality of reservoir surfaces defining a plurality of reservoirs within the larger reservoir (107), such as in a multi-socket design described below.

The wearable system (100) generally includes a rolling element (201) disposed in the at least one first opening (108). As illustrated in FIG. 1e, a plurality of rolling elements (201) may be disposed within the wearable system (100). In this way, the outward facing surface (110) of the system (100) may include a plurality of contact points for dispensing the substance (112) at the convenience of the user. As illustrated, the plurality of rolling elements (201) are situated such that a first portion of the rolling element (210) is outside the base element and a second portion of the rolling element (220) is inside the base element. In this manner, the rolling element(s) (201) are in constant liquid contact with the substance (112) and upon the acting of a threshold amount of external force, the liquid can be transferred from the wearable system to the desired location for the user (e.g., the opposing hand for sanitizing).

Figure 2A:
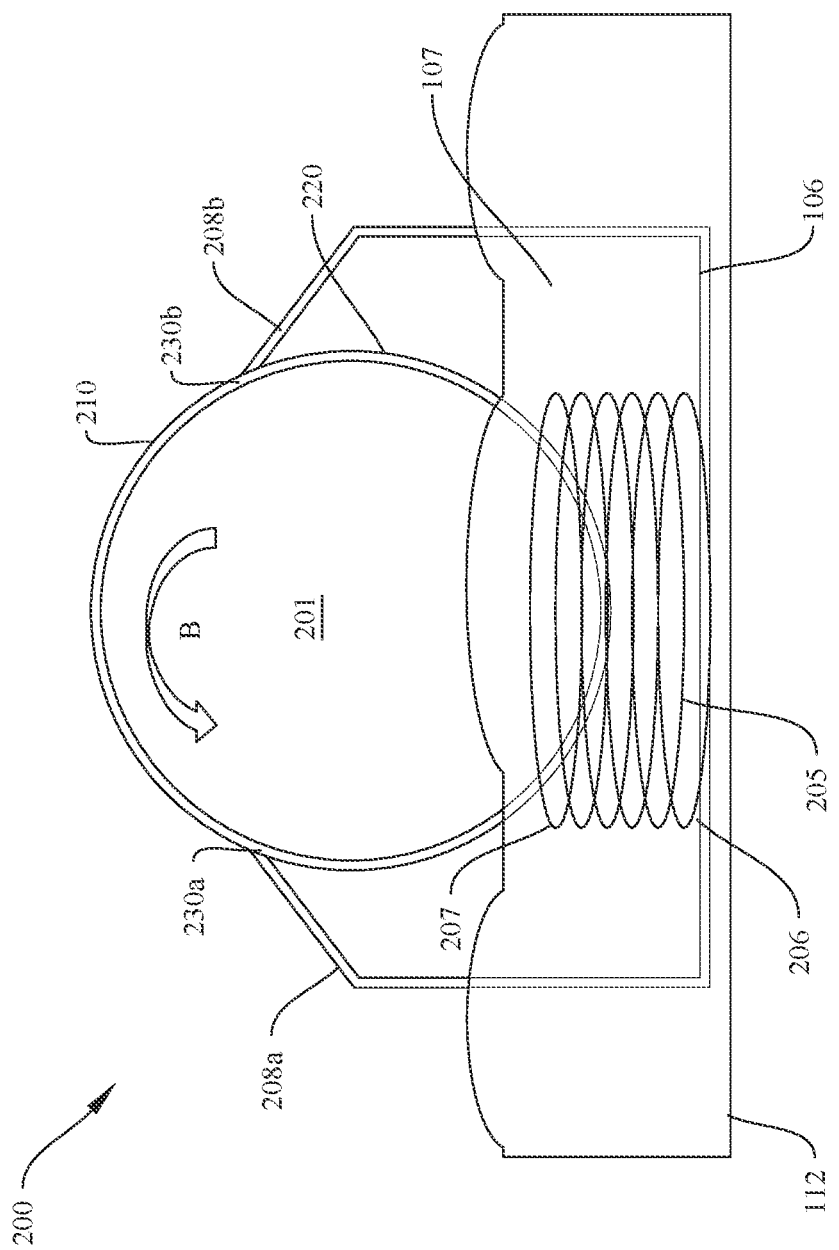
FIG. 2a is a side view of a socket structure in a first position (default position; no forces acting upon the rolling element) to be used in an opening on the outer surface of a wearable system, according to an example embodiment.

With reference to the figures including FIG. 2a, a socket (200) design for containing the rolling element (201) is shown. The socket (200) is shown in a first position, i.e., a default position where no external forces are applied to the outer surface (110) of the wearable system. In this regard, the wearable system generally includes at least one biasing element (205) disposed in the reservoir. The biasing element (205) has a biasing element first end (206) and a biasing element second end (207). The biasing element (205) could be included in such a socket (200) design as illustrated herein. However, other designs where the socket may not be used may also be used and are within the spirit and scope of the invention. As illustrated in FIG. 2a, the rolling element (201) and the biasing element (205) are disposed inside of a socket (200). Such a socket (200) may be disposed within opening(s) (108) described above, and the rolling element (201) is disposed socket (200) to facilitate the transfer of the substance from the reservoir to outside of the wearable system.

The socket (200) may be considered a reservoir, or a part of the larger reservoir inside the wearable system (100). In this regard, the biasing element first end (206) is illustrated as abutting the at least one reservoir surface (106). At the opposing end, i.e., the biasing element second end (207), the biasing element (205) abuts the second portion of the rolling element (220) such that the rolling element (201) is continually biased outward to a first position. Furthermore, the socket (200) includes a retaining wall (208a, 208b) defined by the socket's structure. The retaining walls (208a, 208b) terminate at a third portion of the rolling element (230a, 230b) that abuts the retaining wall (208a, 208b). In this aspect, the first position of the socket design is shown by FIG. 2a. It is understood that a rotational force (line B) may be used to wet the outer surface of the rolling element (201) while in the first position. However, in some instances a user will provide a combination of forces (described below) to facilitate transfer of the substance.

Figure 2B:
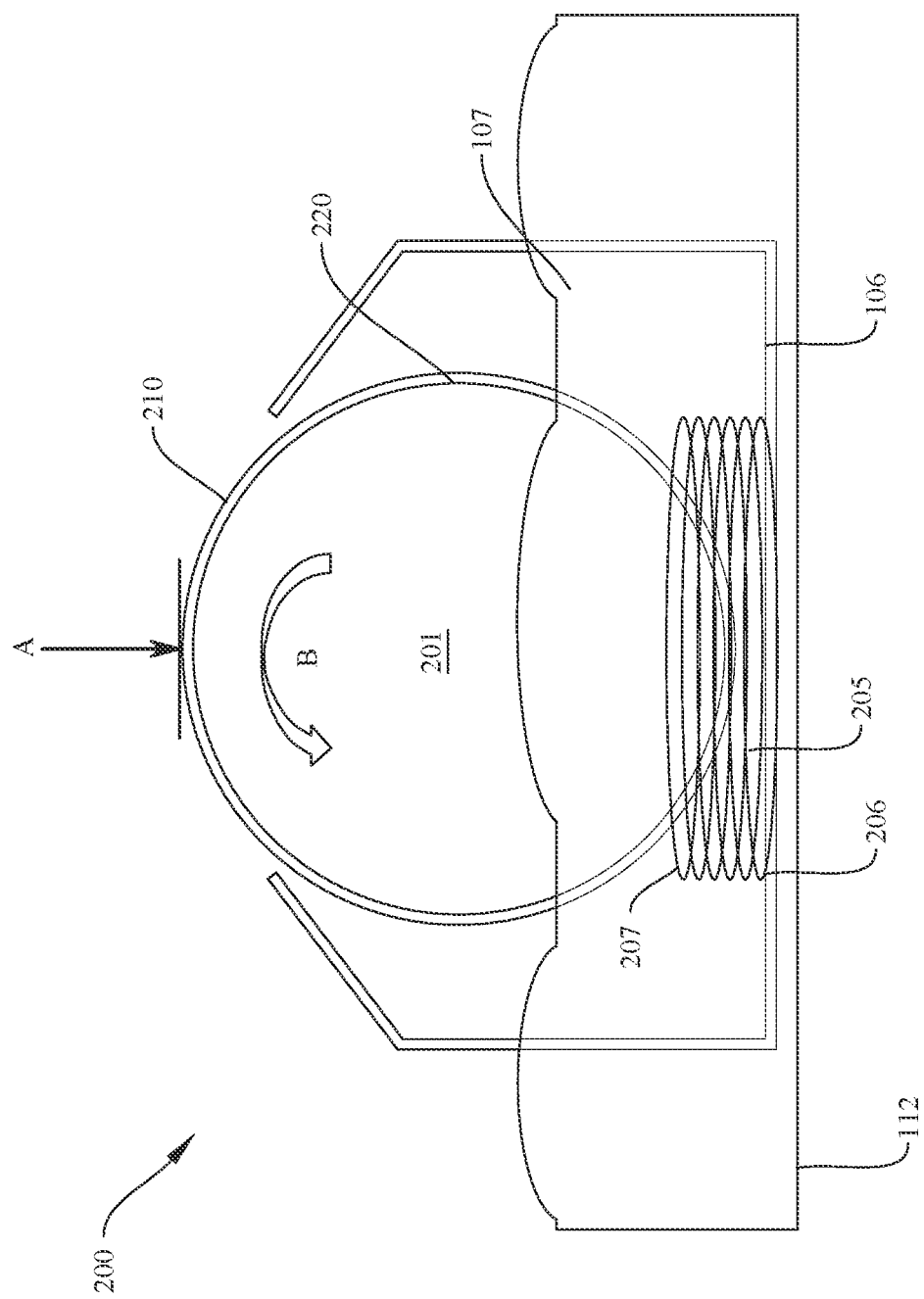
FIG. 2b is a side view of a socket structure in a second position (force-dependent position) to be used in an opening on the outer surface of a wearable system, according to an example embodiment.

With reference now to FIG. 2b, a second position of the (200) socket is shown. Upon the acting of a threshold amount of external force, the rolling element (201) is repositioned to a second position. The term, "threshold amount of external force" refers to the necessary amount of force to cause the rolling element (201) to (i) rotate, (ii) depress by action on the biasing element (205), or (iii) both (i) and (ii). In the second position, the third portion of the rolling element (230a, 230b) may not be in contact with the retaining walls (208a, 208b) of the socket (200) in the second position, thus allowing for the substance (112) to readily dispense through the opening. In this aspect, multiple types of forces may act on the rolling element (201). For instance, downward forces (in the direction of arrowed line A) may act on the rolling element (201) to push the rolling element (201) in the opposing direction of the biasing element (201). This type of force may allow for the contact between the retaining walls (208a, 208b) to be reversed to dispense the substance (112). In another aspect, forces acting orthogonally to the surface of the rolling element (201) (i.e., rotational forces) may be used to dispense the substance (112). For instance, the rolling element (201) may experience such orthogonal forces (i.e., rotational forces in the direction of arrowed line B), thereby rolling the rolling element (201). Rolling the rolling element (201) thereby causes wetted surfaces (with the substance 112) of the rolling element (201) to be exposed to the user for application of the substance. Thus, numerous types of forces may act on the rolling element (201) to dispense the substance (112).

As noted above, the socket (200) or other design may include a biasing element (205). In one embodiment, biasing element (205) is a spring. However, other biasing elements such as magnets, elastics or other polymers may be used and are within the spirit and scope of the present invention.

As noted above, the wearable system (100) may include a reservoir (107) defined by a reservoir surface (106), such as illustrated by FIG. 1d. Reservoir(s) may also be defined by the inside retaining walls (208a, 208b) of a socket (200). As shown in FIG. 1e, a plurality of sockets (200) may be included in the wearable system (100). To facilitate the transfer of the substance from the reservoir (107) to the reservoirs of the sockets (200), each socket may have one or more recessed portions (e.g., holes). For instance, a side view of the socket (200) shown in FIGS. 2a-2b is shown in FIG. 2c. The socket has a hole in the bottom of the socket (200), which is not illustrated. In an alternate socket design (250), one or more holes (255a-255d) may be placed in the retaining wall of the socket structure to facilitate the transfer of the substance from the reservoir (107) to the socket reservoirs. Other shapes and designs of recessed portions may similar be used and are within the spirit and scope of the invention.

Figure 3B:
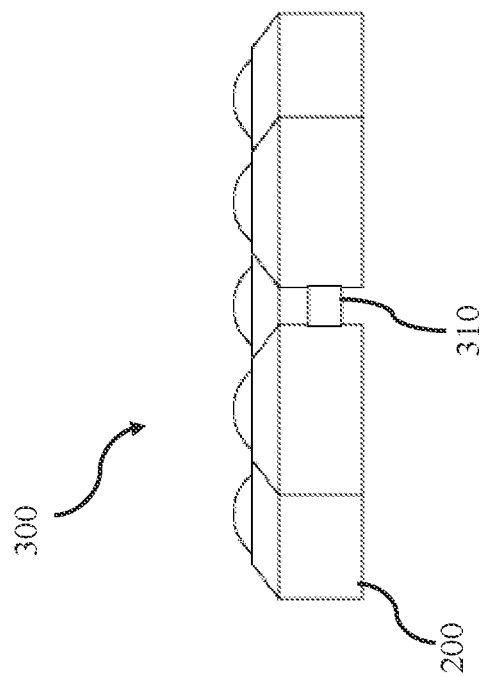
FIG. 3b is a side view of a socket grouping, according to an example embodiment.
Figure 3A:
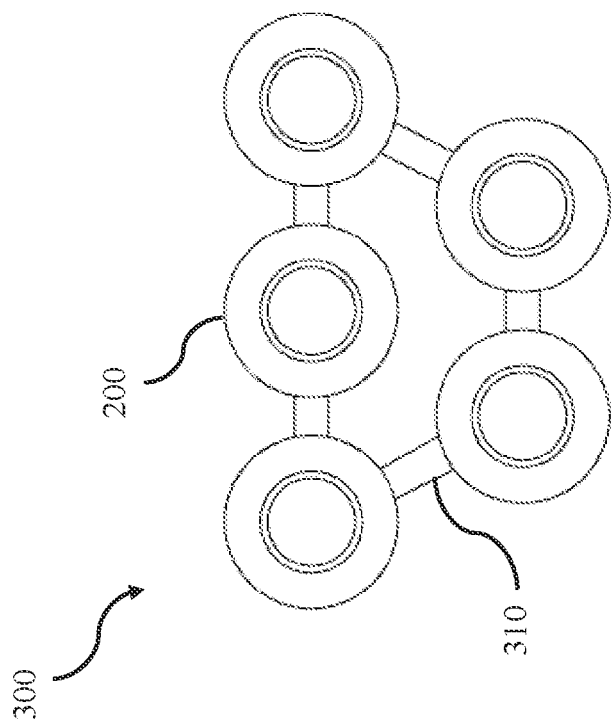
FIG. 3a is a top view of a socket grouping, according to an example embodiment.
Figure 5B:
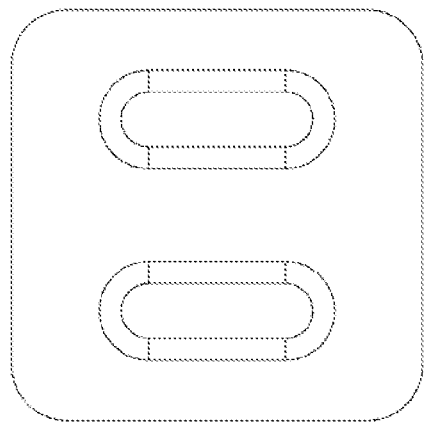
Figure 5A:
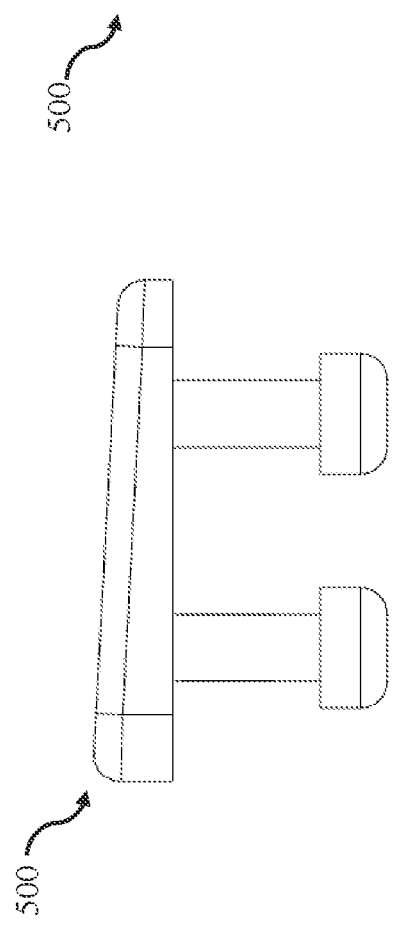
FIG. 5a is a side view of a snap element for securing a wearable system, such as the exemplary elongated band of the preceding figures, in a looped position in accordance with an example embodiment.
Figure 5C:
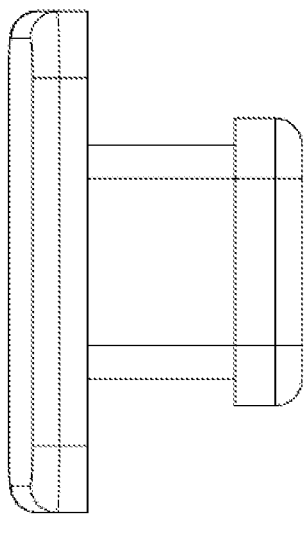

The socket (200) described above may be included in a socket grouping (300) such as shown in FIGS. 3a-3b. The socket grouping (300) may be readily produced and may increase the efficiency of producing wearable systems (100). The socket grouping may include a plurality of sockets (200) that are connected via connectors (310). The socket grouping (300) may be produced by any suitable method, such as by molding, to name one. Since a wearable system (100) may include a significant plurality of sockets (200) (e.g., a dozen or more), producing socket groupings (300) may be preferable due to the reduced effort in assembling the systems (100). Moreover, the connectors (310) may aid in keeping the sockets (200) inside the wearable system (100). For instance, a single socket that is not a part of a socket grouping may "pop out" of the system (100) when the system is flexed, due to the flexible properties of the device. Thus, in some embodiments a wearable system (100) includes at least one socket grouping (300), where the socket grouping (300) includes at least two sockets (200) connected by at least one connector (310), which aids in keeping the socket in position and preventing the sockets from "popping out."

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

We claim:

1. A wearable system for dispensing a substance comprising:
   a base element;
   at least one reservoir surface defining a reservoir disposed in the base element;
   at least one first opening disposed along on an outward facing portion of the base element and providing fluid communication with the reservoir; and
   a rolling element disposed in the at least one first opening such that a first portion of the rolling element is outside the base element and a second portion of the rolling element is inside the base element.

2. The wearable system of claim 1, wherein the wearable system further comprises:
   a biasing element disposed in the reservoir, the biasing element having a biasing element first end and a biasing element second end;
   wherein the biasing element first end abuts the at least one reservoir surface;
   wherein the biasing element second end abuts the second portion of the rolling element such that the rolling element is continually biased outward to a first position; and
   wherein the rolling element moves into a second position when a threshold amount of external force acts on the rolling element.

3. The wearable system of claim 1, wherein the wearable system further comprises:
   at least one socket structure disposed within the at least one first opening;
   a retaining wall defined by each of the at least one socket structure; and
   wherein a third portion of the rolling element abuts the retaining wall of each of the at least one socket structure when (i) the at least one socket structure is disposed within the at least one first opening, (ii) the rolling element is disposed within the at least one socket structure and (iii) the rolling element is in a first position.

4. The wearable system of claim 1, wherein the base element is an elongated band.

5. The wearable system of claim 1, wherein the base element comprises a second opening disposed on the outward facing portion of the base element, the second opening providing fluid communication with the reservoir.

6. The wearable system of claim 5, wherein a cover is configured for closing the second opening.

7. The wearable system of claim 6, wherein the cover is hingedly in attachment with the base element.

8. The wearable system of claim 4, wherein the elongated band has a first end and a second end, wherein the first end of the elongated band is configured to removably attach to the second end of the elongated band to form a looped element to be worn on a user's wrist.

9. A wearable system for dispensing a substance comprising:
   (a) a base element, wherein the base element defines an elongated band;
   (b) at least one reservoir surface defining a reservoir disposed in the base element;

(c) at least one first opening disposed along on an outward facing portion of the base element and providing fluid communication with the reservoir;
(d) a rolling element disposed in the at least one first opening such that a first portion of the rolling element is outside the base element and a second portion of the rolling element is inside the base element;
(e) at least one socket structure disposed within the at least one first opening;
(f) a retaining wall defined by each of the at least one socket structure; and
wherein a third portion of the rolling element abuts the retaining wall of each of the at least one socket structure when (i) the at least one socket structure is disposed within the at least one first opening, (ii) the rolling element is disposed within the at least one socket structure and (iii) the rolling element is in a first position.

10. The wearable system of claim 9, wherein the wearable system further comprises:
a biasing element disposed in the reservoir, the biasing element having a biasing element first end and a biasing element second end;
wherein the biasing element first end abuts the at least one reservoir surface;
wherein the biasing element second end abuts the second portion of the rolling element such that the rolling element is continually biased outward to the first position; and
wherein the rolling element moves into a second position when a threshold amount of external force acts on the rolling element.

11. The wearable system of claim 9, wherein the base element comprises a second opening disposed on the outward facing portion of the base element, the second opening providing fluid communication with the reservoir.

12. The wearable system of claim 11, wherein a cover is configured for closing the second opening.

13. The wearable system of claim 12, wherein the cover is hingedly in attachment with the base element.

14. The wearable system of claim 9, wherein the elongated band has a first end and a second end, wherein the first end of the elongated band is configured to removably attach to the second end of the elongated band to form a looped element to be worn on a user's wrist.

15. A wearable system for dispensing a substance comprising:
(a) a base element;
(b) at least one reservoir surface defining a reservoir disposed in the base element;
(c) at least one first opening disposed along on an outward facing portion of the base element and providing fluid communication with the reservoir;
(d) a rolling element disposed in the at least one first opening such that a first portion of the rolling element is outside the base element and a second portion of the rolling element is inside the base element;
(e) a biasing element disposed in the reservoir, the biasing element having a biasing element first end and a biasing element second end;
wherein the biasing element first end abuts the at least one reservoir surface;
wherein the biasing element second end abuts the second portion of the rolling element such that the rolling element is continually biased outward to a first position;
wherein the rolling element moves into a second position when a threshold amount of external force acts on the rolling element;
(f) at least one socket structure disposed within the at least one first opening;
(g) a retaining wall defined by each of the at least one socket structure; and
wherein a third portion of the rolling element abuts the retaining wall of each of the at least one socket structure when (i) the at least one socket structure is disposed within the at least one first opening, (ii) the rolling element is disposed within the at least one socket structure and (iii) the rolling element is in the first position.

16. The wearable system of claim 15, wherein the base element is an elongated band.

17. The wearable system of claim 15, wherein the base element comprises a second opening disposed on the outward facing portion of the base element, the second opening providing fluid communication with the reservoir.

18. The wearable system of claim 17, wherein a cover is configured for closing the second opening.

19. The wearable system of claim 18, wherein the cover is hingedly in attachment with the base element.

20. The wearable system of claim 16, wherein the elongated band has a first end and a second end, wherein the first end of the elongated band is configured to removably attach to the second end of the elongated band to form a looped element to be worn on a user's wrist.

* * * * *